United States Patent [19]

Stube

[11] 4,386,707
[45] Jun. 7, 1983

[54] LASER BEAM IMPERFECTION DETECTION FOR PLASTIC FILM ROLLS

[75] Inventor: Steven H. Stube, Midland, Mich.

[73] Assignee: The Dow Chemical Company, Midland, Mich.

[21] Appl. No.: 250,380

[22] Filed: Apr. 2, 1981

[51] Int. Cl.³ .............................................. B07C 5/00
[52] U.S. Cl. .................................. 209/546; 209/579; 250/563; 250/572; 250/358.1; 356/237
[58] Field of Search ............... 209/579, 546, 549, 550; 356/237, 429, 430, 431, 239; 250/358 R, 223 R, 562, 563, 572, 358 P

[56] References Cited

U.S. PATENT DOCUMENTS

| | | | |
|---|---|---|---|
| 3,565,536 | 2/1971 | Wuellner et al. | 356/239 |
| 3,652,863 | 3/1972 | Gaskell et al. | 356/239 X |
| 3,690,774 | 9/1972 | Kottle et al. | 356/239 X |
| 3,804,534 | 4/1974 | Clarke | 356/237 |
| 3,812,349 | 5/1974 | Gugliotta | 209/579 X |
| 3,843,890 | 10/1974 | Anthony, Jr. et al. | 356/239 X |
| 4,136,779 | 1/1979 | Bieringer | 209/579 X |
| 4,162,125 | 7/1979 | Schmidt | 356/239 X |
| 4,208,126 | 6/1980 | Cheo et al. | 356/239 X |

Primary Examiner—Allen N. Knowles
Attorney, Agent, or Firm—R. B. Ingraham

[57] ABSTRACT

A system for non-destructive, non-contacting use for detecting imperfections in multi-layered supply rolls of wound plastic film comprises a laser which scans the length of the particular roll being inspected with a photo-electric detector at a fixed reference angle which picks up reflected unimpeded and scattered light plus associated indicating and/or recording equipment. Defects in the roll, particularly those related to the upper longitudinal surface thereof, cause light scattering which decreases the signal strength to the indicator or recorder, thus noting the presence of a wrinkle or the like imperfection in the film roll.

14 Claims, 13 Drawing Figures

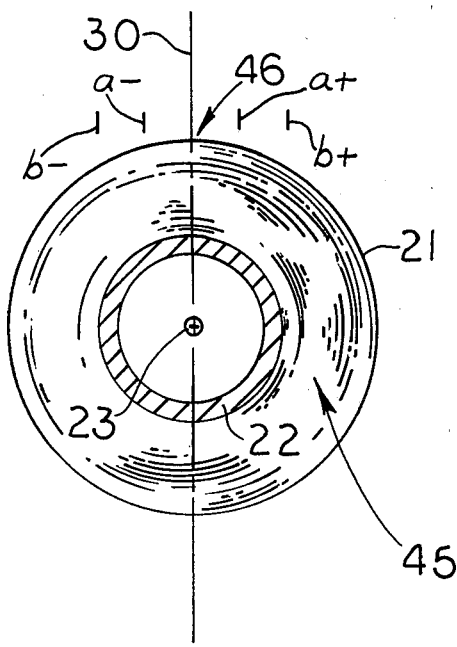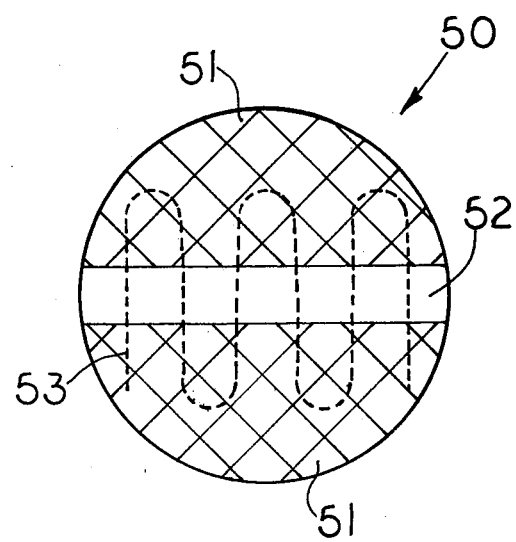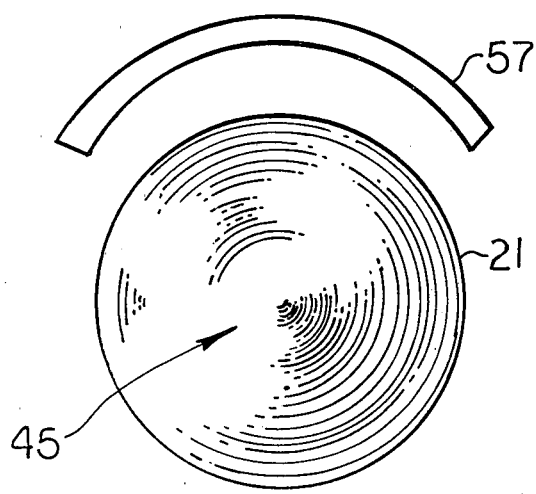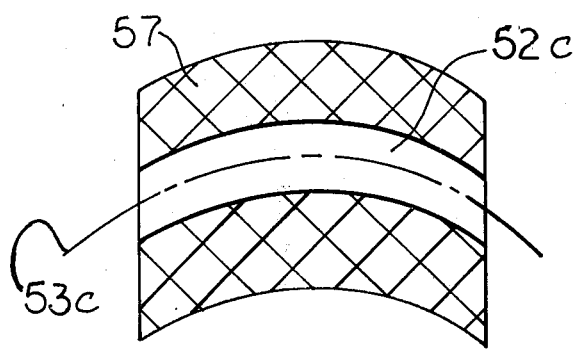

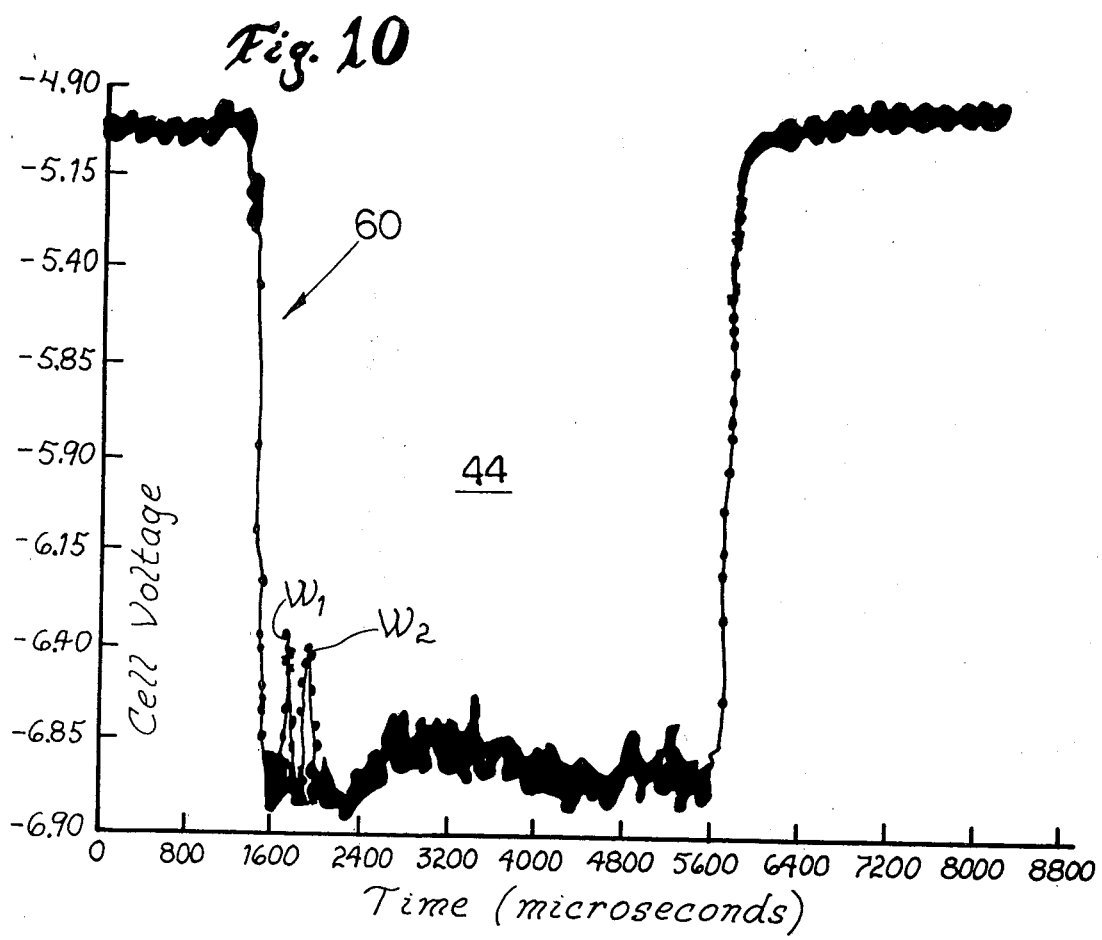
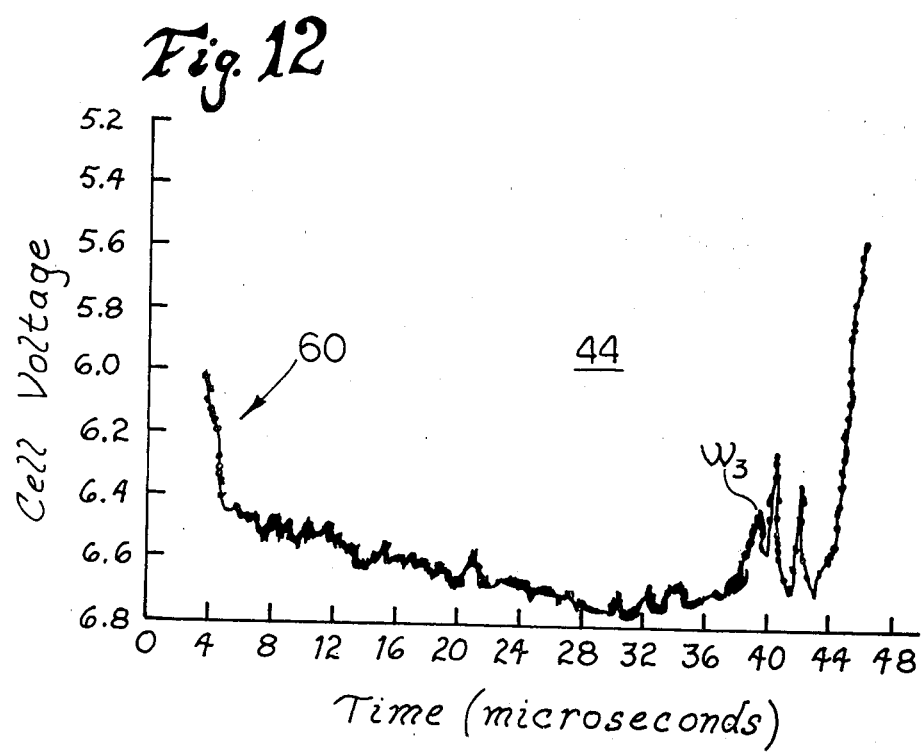

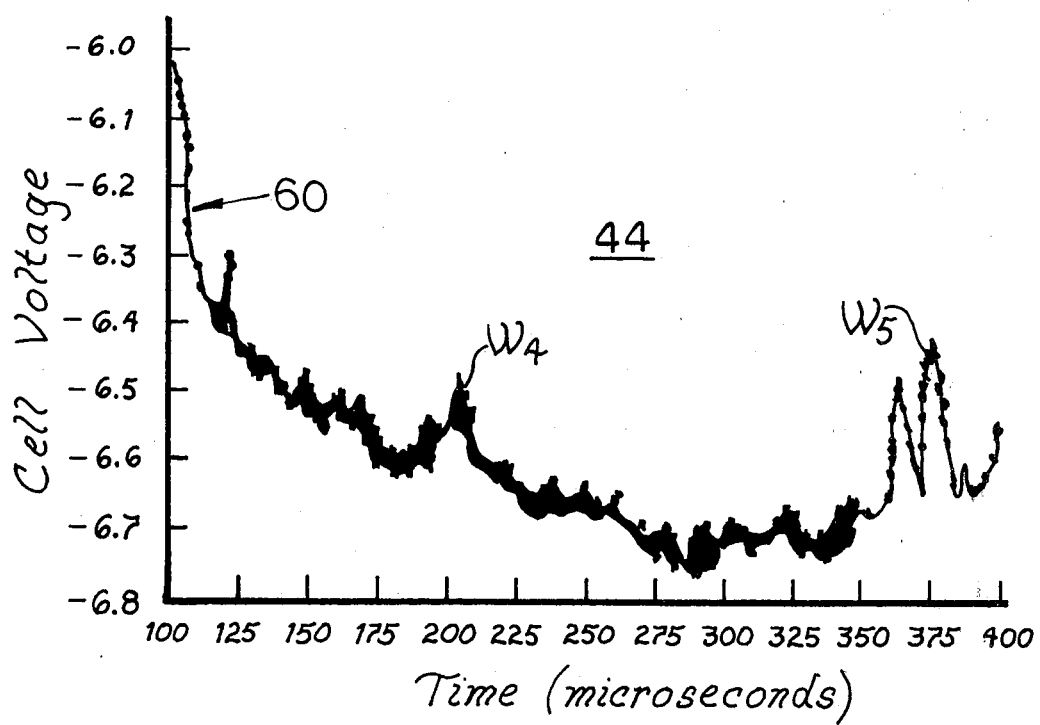

LASER BEAM IMPERFECTION DETECTION FOR PLASTIC FILM ROLLS

BACKGROUND OF THE INVENTION

Literally needless to emphasize, serious defects in wound or wrapped, multilayer supply rolls of various plastic film products arise from various wrinkles (including the so-called "knots" caused by large wrinkles as well as small, hard wrinkles in the rolled-up film product), die lines, seams, air knife and the like lines, foreign material(s) included in the wrapping plies, etc. These, upon attempted dispensation of such imperfectly wound roll packages, tend to cause tearing into strips of the film end being released from the supply or, in even more drastic consequence, complete failure of film dispensing capability.

As limited and restricted as it is, the presently known and utilized technique for quality control testing of wrinkles in wound supply rolls of plastic film by and large consists of visual spot checking which, unavoidably, is subject to qualitative and personalized judgment. In such procedure, correlations between wrinkle (and other imperfection size) and product failure in the indicated particulars have ordinarily been incapable of achieving overall or 100 percent on-line roll inspection concluding of the manufacturing process.

Typical of the plastic films involved in such manufacturing quality control difficulties are "HANDI-WRAP" TM Brand polyolfin film and "SARAN WRAP" TM Brand saran film, both of which are commercially made by and available from The Dow Chemical Company of Midland, Mich. 48640. Of course, many other analogous and similar plastic film products are beset by the same problems insofar as concerns quality control procedures in their manufacture.

There are a number of known arrangements in which laser beams are utilized for quality control and flaw-detection purposes in various materials, including plastic goods. Among these are those shown in U.S. Pat. Nos.: 3,771,171 (to Hollenbeck); 3,792,930 (to Obenreder); 3,807,870 (to Kalman); 3,843,890 (to Anthony et al.); 4,017,194 (to Conroy et al.); 4,136,961 (to Young); 4,162,125 (to Schmidt); 4,197,457 (to Cheo); and 4,208,126 (to Cheo et al.).

Of these, the Patent to Cheo et al.; the same pertaining to the detection of flaws in polyethylene insulated cable through the use of a laser and a detector. The Cheo reference is somewhat more generally directed to the subject of detecting flaws in plastics, again with use of a laser and a detector.

Nothing in the prior art, however, appears to realistically concern itself with nor teach nor lead to an effective, efficient and extremely reliable means and technique, well-adapted for production line application and usage, for accurate wrinkle and other flaw testing in quality control inspection and observation of wound supply rolls of plastic film product using laser beam means in the implementation as in the way so crucially indigenous as is in the present contribution to the art.

FIELD AND PURVIEW OF THE INVENTION

The present invention, and the principle aims and objectives attainable in its practice, pertain(s) and direct(s) to a novel and, in the overall, unprecedented and exceptionally efficient means and technique for quickly and efficaciously inspecting wound plastic film supply rolls so as to allow 100 percent checking of output from a given product line by non-destructive assessment so as to reliably find wrinkles and other deleterious and undesirable flaws and imperfections in the roll-packaged goods before attempted distribution and/or use thereof.

The achievement and provision of all indicated, with even more and additionally other benefits and advantages derivable in and from present practice appear and become more evident in the ensuing description and Specification.

SUMMARY OF THE INVENTION

The present invention, in its genesis and as derives from the discovery on which it is based, pertains to the indicated novel means and technique which comprises, in cooperative combination assembly as a system for quality control test detection of wrinkle and other imperfections in a plastic film supply roll without physical contact or destruction thereof: a multiply-layered, convolutely wound supply roll of a plastic film; means for mounting said supply roll in longitudinally-extending dispostion along its axial center line in the assembly; means for generating a laser beam of electromagnetic radiation at a given wavelength; means for directing said laser beam into said supply roll along a path that is incident to and at a predetermined angle of orientation with respect to said supply roll so as to impinge at least substantially through and within a normal, upright plane that at least about intersects said center line of said supply roll; such that any portion of said laser beam which passes through the multiple layers of said supply roll unobstructed by wrinkles or analogous structurally imperfect defects in the multiple film layers does so along a predictable and precisely deflected and reflected and unimpeded path; and any portion of said laser beam which impinges one of said wrinkles or the like defects is thereby scattered along predictable scattering paths including paths different than said unimpeded path; means for picking up and indicating the unimpeded and impeded laser beam reflections whereby to detect and indicate through an intelligent reporting appliance any of said scattered electromagnetic radiations caused by said wrinkle and the like impediment(s); and means for causing said laser beam to longitudinally sweep and scan the longitudinal length of said supply roll.

Method usage, as implied, of the contemplated means assembly is also here envisaged and intended as an integral part of the invention.

Still other features and implementations of beneficial import and salience and advantageously combinable in and made integral part(s) of the basic and above-fundamentally-delineated efficient means for quality control of plastic film rolls pursuant to the invention.

Thus, various suitable parts, elements, sub-assemblies and overall assemblies plus other equipage for utilization, as well as working details, embodimental instructions and parameters and other specifics of the invention are also set forth in the following Specification.

ILLUSTRATED EXEMPLIFICATION OF THE INVENTION

The invention is pictorially demonstrated in and by the thirteen (13) views of the accompanying Drawing (a number of which, for simplicity and convenience, are illustrated in somewhat schematic and/or fanciful manner of representation and some of which are graphical, data-depicting portrayals and all of which insofar as possible utilize the same reference numerals and letter designations for like and/or similar parts and/or elements and/or movements) wherein, as they are to be taken in conjunction with the Specification that follows.

Figure 3:
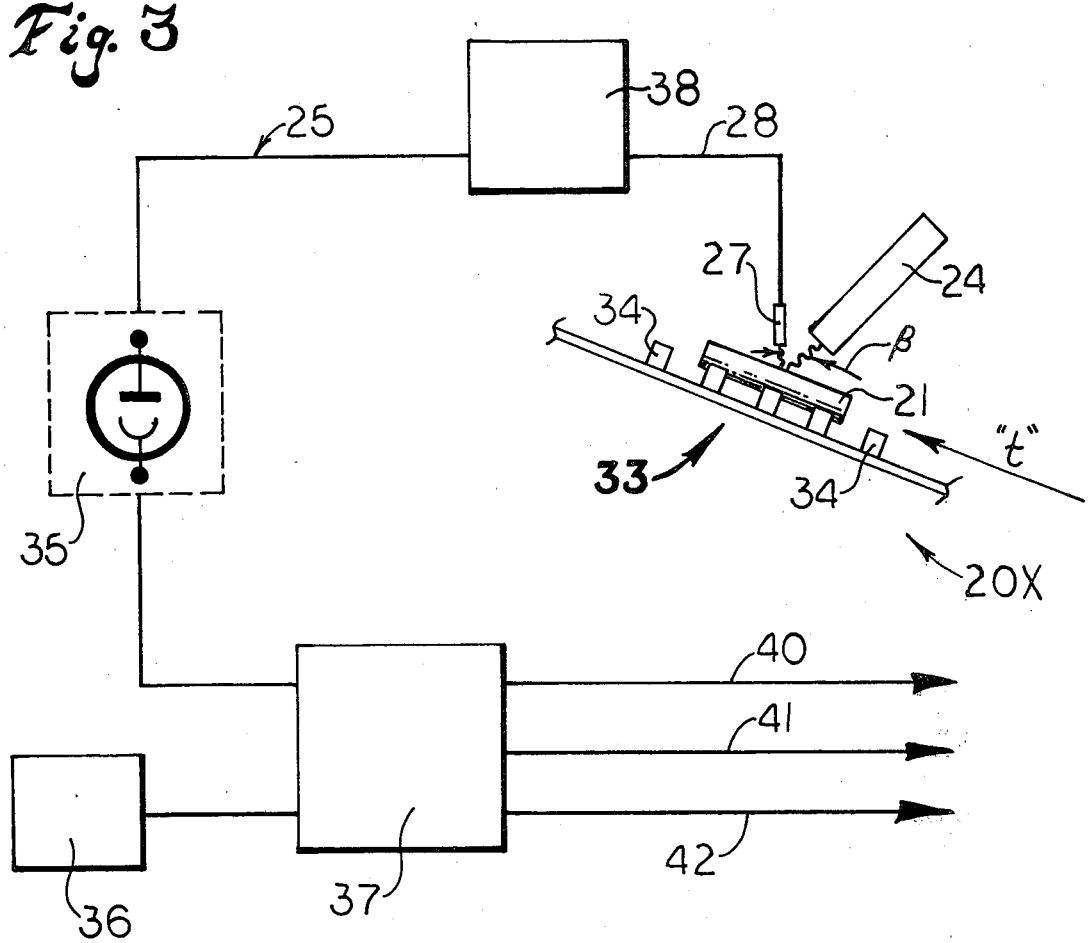
Figure 4:
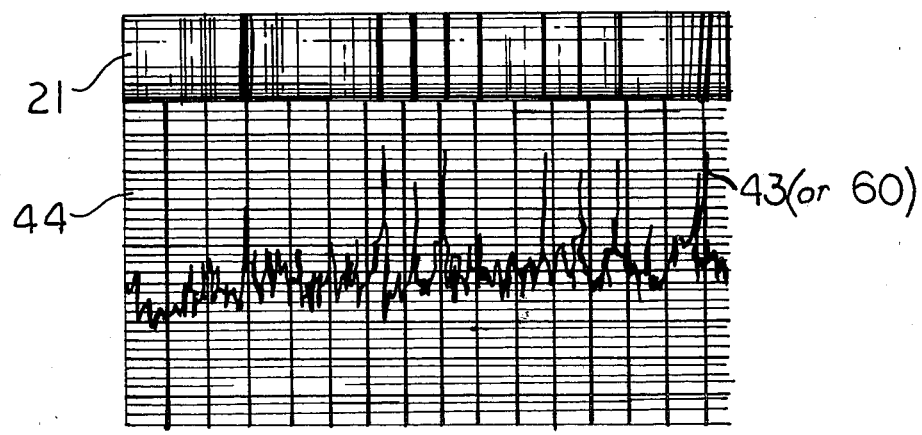
Figure 6:
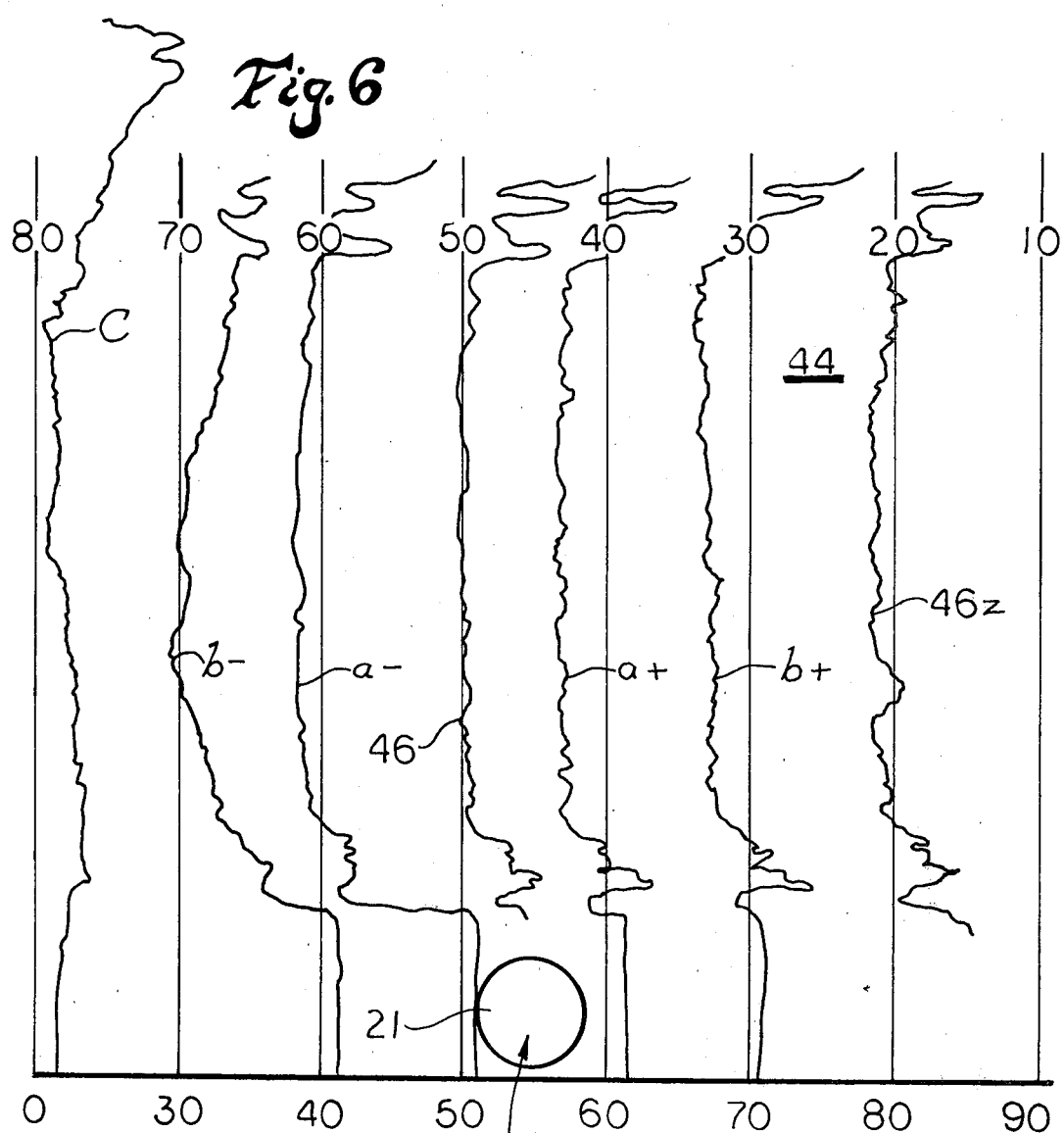
Figure 11:
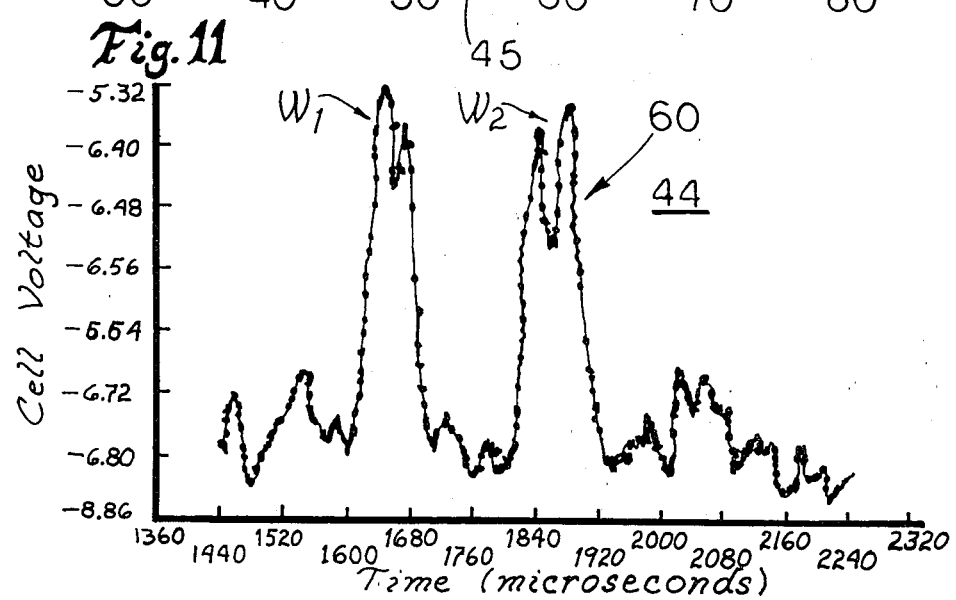

FIG. 3, in schematic, flow-layout sort of diagrammatic presentation, sets forth an overall combined electrical and mechanical embodimentation of an assembly pursuant to the invention with advantageously varied laser beam scanning implementation therein incorporated;

FIG. 4 is a representation in plan view analogy of a chart paper product demonstrating imperfection representations in the graph thereon in relationship to the plastic film roll tested for the recorded indication;

FIG. 5 is a fanciful end view elevation of a wound supply roll of plastic film to be tested bringing forth some important positions on the roll for optimum laser beam scan readings thereof during a quality control inspection thereon;

FIG. 6 is a graphical representation of recorded data procured in scans run along the several positions indicated in FIG. 5;

FIG. 7, in front plan view fanciful representation, shows one way of masking a photo detector unit in an assembly set up in keeping with the invention so as to provide more selective reception thereby of scattered laser beam light reflected from various positions at and about the crown or uppermost peripheral tangent line of a longitudinally-disposed roll being subjected to test;

FIG. 8, in schematic end-view perspective, illustrates an advantageous curvilinear structural form of a so-called "solar" beam detector for utilization in an assembly for practice of the instant invention;

FIG. 9, in a manner of presentation similar to that set forth in FIG. 7, demonstrates advantageous masking of the curvilinear detector of FIG. 8 (as seen in the view with its top tilted forward into line of sight); and FIGS. 10 through 13, inclusive, are reproductions of graphs obtained on recorder chart paper provided from quality control tests of wound plastic film supply rolls showing wrinkle and other imperfection.

For expedience and enhanced clarity of associated parts, elements; components; subassemblies and assemblies; certain companion movements, functions and so forth; and results, reference is now thereto had to all such predominant cooperative componential features and consequences of their operation as they appear throughout the accompanying Figures included in the Drawing with explanation thereof in the following cataloged description of same as they are identified by their respective reference numeral(s) or letter designation(s) (i.e., "Ref. No(s).") therewith joined.

Figure 1:
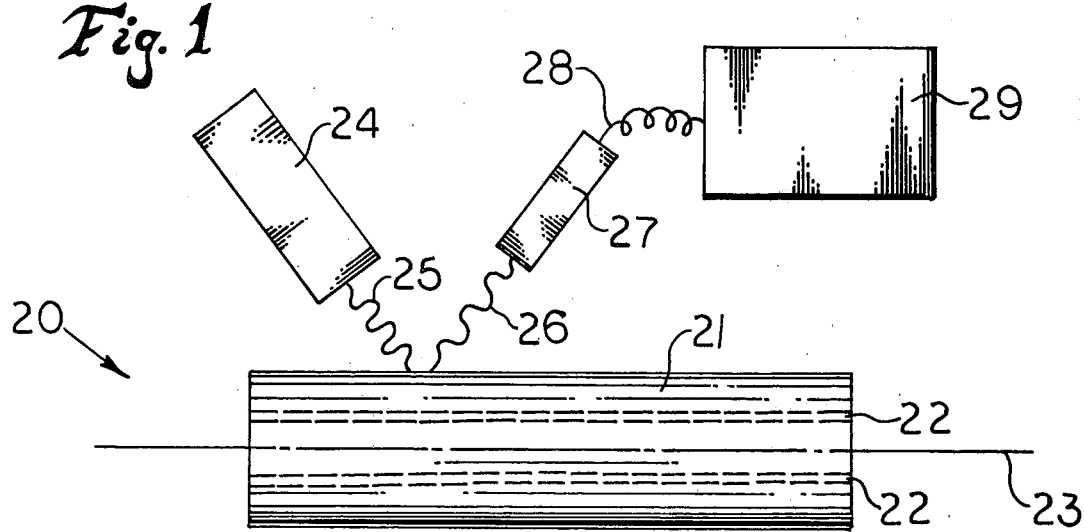
FIG. 1 is a generalized, relatively symbolic and fanciful side elevation view showing in broad overlook the major details and salient functional elements of a laser beam plastic film roll inspection assembly in accordance with the present invention.
Figure 2:
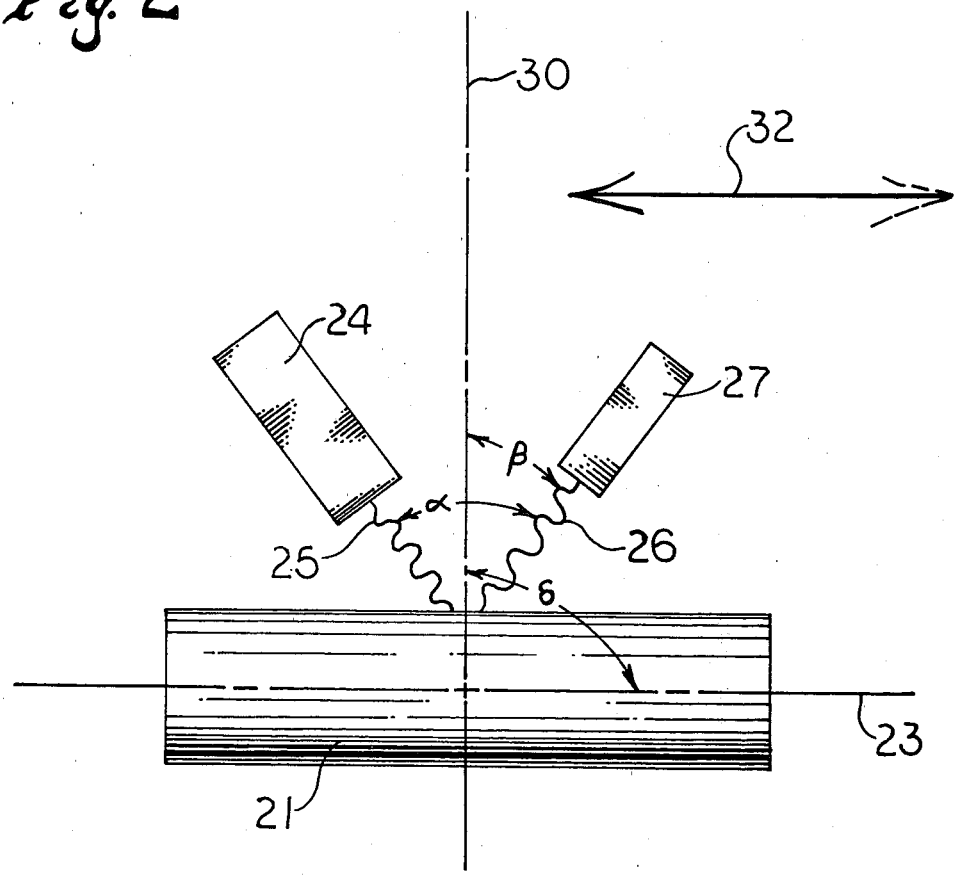
FIG. 2 is a view analogous to that of FIG. 1 with some elimination of components and some supplementing illustration of key arrangements to be effected in the assembly.

| Ref. No(s). | Description With Relevant Corollary Explanation |
|---|---|
| 20 | General designation of laser beam/detector, etc. assembly set up for practice of the present invention. |
| 21 | A multiply-layered, convolutely wound, supply roll of plastic film. |
| 22 | The support core (in section in FIG. 1) for the film supply roll. |
| 23 | The axial longitudinally-extending center line of supply roll 21. |
| 24 | The laser beam generating unit, advantageously of the helium-neon type. |
| 25 | The transmitted laser beam directed to angularly impinge at or along the uppermost surface or crown of the supply roll 21. |
| 26 | The reflected laser beam path or line of direction after roll deflection. |
| 27 | An appropriate photo detector for picking up the reflected beam 26. |
| 28 | Electrical wire connection(s). |
| 29 | A suitable recorder for visually and/or graphically translating into graphical or equivalent representations discernible by the eye (or other desired intelligence gathering and handling device). |
| 30 | The "normal" or perpendicular line relative to and intersecting center line 23 of the supply roll 21. |
| 32 | Bidirectional arrow (shown only in FIG. 2) to depict the movement parallel to the axis (or center line 23) of a supply roll 21 being tested of a movable carriage (not shown) to support the laser beam generator and detector unit for scan implementation and direction when a stationary supply roll is undergoing observation. |
| δ | The 90° angle between center line 23 and the "normal" line 30 which is thereto perpendicular. |
| α | The angle between the generated laser beam 25 line or path of direction and the reflected path line 26 of the deflected beam from the roll. |
| β | The angle between perpendicular line 30 and reflected laser beam path line 26; the value of β being ½ that of α and ordinarily (although other angulations may be utilized) being most advantageously on the order of about 20° (i.e., when α is 40°). |
| 20X | General designation (indicated in FIG. 3) of an overall assembly in accordance with the invention in which the plastic film roll being tested is longitudinally moved (as in a production line station for the purpose) to provide the scanning effect relative to a stationarily-positioned laser beam/detector unit. |
| 33 | General designation (again, indicated in FIG. 3) of a broken-out schematically-depicted plastic roll conveyor system to pass the rolls under the laser beam so as to thereby obtain the scanning effect. |
| 34 | Mechanical roll-aligning belt cleats. |
| 35 | Photo-cell light beam installation and circuit (actually positioned with functional relativity to the roll conveyor system 33 in the assembly plan 20X of FIG. 3) to indicate roll-in-place for testing orientation and roll size being tested. |
| 36 | Electronic program input unit to accommodate the test manner and sequence being conducted. |
| 37 | Micro (or equivalent) computer installation to handle data input for control purposes and data output for indicating and/or recording purposes. |
| 38 | "Oriel" control box unit with electronic trigger circuitry therein contained. |
| 40 | "Yes" (when objectionable defect level in roll being tested is present)/"no" (when satisfactory roll is indicated) trans-positor sort of ejector (relay) circuitry and system to remove undesirable and/or bad product rolls from production line and inclusion amongst goods considered as having acceptable suitability and quality. |
| 41 | Recorded (or recording or other intelligence conveying) output signal line. |

-continued

| Ref. No(s). | Description With Relevant Corollary Explanation |
| --- | --- |
| 42 | Report line (or other equivalent intelligence signal output). |
| 43 & 44 | Traced curve line 43 (or 60) and chart paper reproduction 44, respectively. |
| "t" | Direction of roll conveyance or travel-indicating arrow (in FIG. 3) |
| 45 | General designation of end of wound film roll 21. |
| 46 | General designation of crown or uppermost tangent line point parallel to center line 23 on topside peripheral surface of wound film layers in supply roll 21. |
| a+ | Positive, 0.050 inch (ca. 0.127 centimeter) offset displacement mark relative to crown point 46 (brought forth, as with marks a−, b+ and b− described below, in connection with FIGS. 5 and 6 of the Drawing). |
| b+ | Positive, 0.100 inch (ca. 0.254 centimeter) offset displacement mark. |
| a− | Negative, 0.050 inch offset displacement mark. |
| b− | Negative, 0.100 inch offset displacement mark. |
| C | Control line graph in the chart duplicated in FIG. 6. |
| 46z | Measurement line recorded and shown in FIG. 6 with the tail of the wound supply roll 21 (i.e., the portion in the outermost wrapped layer) embossed on the surface for test measurement purposes. |
| 50 | General designation of the face of a photo-cell detector unit. |
| 51 | Masked area(s) of face of photo-cell 50. |
| 52 | Detection cell in face of photo-cell unit 50 with masked areas 51 thereon in place. |
| 53 | Pattern trace line as at least imaginarily appears in photo-cell (50) face. |
| 57 | Curved so-called "solar" reflected laser beam detection cell for use in an assembly in accordance with the invention. |
| 52c | Curved detection slit in solar cell 57. |
| 53c | Curvilinear appearing center line in curved solar cell unit 57 in tilted aspect. |
| 60 | General designation of traced, imperfection-revealing curve as appears on recorded line of chart paper. |
| $W_1, W_2$ $W_3, W_4$ | Wrinkle point appearances in curve line(s) 60 recorded on chart paper to be correlated with wrinkles, etc., and other defects and flaw imperfections in plastic roll undergoing quality control testing pursuant to the invention. |

With an overview of the several depictions, views and illustrations of the Drawing being maintained (especially in the light of the foregoing explanation of parts, components, etc., and other elucidations), the subsequent portion of this Specification now turns to a somewhat more cohesive and particularlized disclosure and exposure of and coordinated amplification upon the invention; including therein most appropriate and expedient (or best) manners and means stemming from the foregoing in which the same way be advantageously and propitiously embodied and practiced.

In this connection, the basic principles and limitations of: plastic film and wound supply rolls thereof; mechanisms for providing same; laser beam electromagnetic radiation generation and handling and utilization of paths (including deflected and reflected, as well as scattered-beam, paths thereof); photo detectors of various styles, types and capabilities including those for use with laser beams; recording and intelligence-relating and transmitting devices and apparatus; computer and electric and electronic control units; mechanical scanning means and devices; mechanical product selection and rejection installations to be utilized in connection with automatic product quality control procedures; machine and machine parts design and implementations(s) for the presently-contemplated purpose; suitable materials of construction for given utilization requirements; and so forth are so widely comprehended by those skilled in the art that greatly elaborated detailing and/or fundamentals-explanation of all the basics thereof is not herein made or attempted; the same being unnecessary for thorough understanding the recognition of the advance possibilitated for achievement and realization by and with the development in and for an outstanding wrinkle and the like analogous flaw imperfection detection and quality control inspection cooperative assembly combination(s) improvement that is according to and in keeping with the present invention.

PARTICULARIZED OPERATION AND USE DESCRIPTION OF THE INVENTION

As is clearly evident in and readily-enough deducible from the foregoing disclosure and description, the present invention in basic essence and substance contemplates the provision for use of a laser beam outfit for an innovative wrinkle and other objectionable flaw detection quality control assembly with and upon multiply-layered, wound supply rolls of conventional and other plastic films, including those currently in common usage and widespread commercial provision. The laser beam scanning arrangement thus readily achieves practical and effective inspection techniques and arrangements which, quite nicely and handily, may be incorporated in production line set-ups to discard unwanted and undesirable units of the plastic film rolls being made; this, if desired, without overly difficult implementation being possible to embody on fully automatic and assembly-controlled and -operated installations where even human inspection activity may be unnecessary of item-by-item viewing involvement.

Some of the characteristics and particulars of the instant contribution to the art that are, perhaps, not completely-abundantly-plain in and from the foregoing Specification are not more precisely expostulated, including some optimum features prescribable for practice of the invention.

The basic and outstanding advantage and hitherto unknown benefit of the present invention is the exceptional adaptability and latitude it allows of and for ready, non-destructive, non-contacting inspection for quality control of plastic film rolls prior to actual wound product commercial (or other) distribution and outlet. This, by virtue of the instant development, allows such regulation to be done literally instantaneously or, as it were, "on the fly" in a production line without encountering for such purpose any uncertainties due to sheer visual inspections or requiring any wound product disruption techniques to ascertain the presence of undesirable defects in given wound supply packages being made of the involved plastic film as the applied operating technique for the culling of problem rolls.

Accordingly and as has been pointed out, the laser beam is caused (by one or another appropriate mechanism thereabout associated) to scan the length of the roll to be inspected. During this time, the photo-cell detector which is set at a fixed reference angle picks up reflected light of the beam first generated and directed at an incident angle upon the top of the roll being examined. Suitable recording means is/are utilized to indicate the amount of light picked up (or "seen") by the detector. Wrinkles and the like or equivalent or other flaws and defects, both on the surface and in or within the multiply-layer wraps of the wound plastic film supply roll, cause light scattering of the impinging laser beam being reflected. This, as the scattering occurs, decreases the signal strength to the photo-detector and associated recording means so as to thus indicate the existence of a perceptible defect.

A resistance versus time trace (or its like or equivalent) can be reproduced from this by any suitable means (including on video screens but preferably by a recorded curve on a graphed chart paper) which, in calibration with the given scan speed being employed, indicates the location of any and all defects in the roll. The magnitude (including associated distortion) of the signal and its duration indicates height and width of the involved defect, as each of these denotations are respectively given and observable. This information can be advantageously used to eliminate or cull problem rolls which are those, according to any desired standard to apply, which have defects of sufficient and usually size character so as to give usually predictable dispensing or other associated problems.

As a demonstration of this, attention is again called to the data represented in FIG. 4 of the Drawing. To obtain this (and as was done in an off-production-line test), a roll of commercial household "HANDI-WRAP" TM polyolefin film was chucked up in a lathe bed. A laser beam generator and detector unit was set up on a movable carriage over the roll in general following of the indications of FIGS. 1 and 2 of the Drawing. Angle $\alpha$ in this deployment was approximately 40°, with the generated laser beam having been scanned parallel to the roll length so as to impinge during scanning upon the crown thereof. The output of the photo-detector was fed to a recorder. The trace thereby generated was, as is shown in FIG. 4, exactly compared to roll length. From the trace, detection of defect(s) severity was indicated from various spike heights and severities in the curve 43 on chart paper 44. If the indicated defects were sufficiently intense and objectionable (as was the case in the described illustration) the roll should be culled and deleted from distribution as a satisfactory product.

Associated with FIGS. 5 and 6 of the Drawing were tests run to determine the significance of different quantities of physical space offset from the crown of the roll with respect to impingement on the roll of the generated laser beam to be reflected therefrom. This was performed with wound supply rolls of "SARAN WRAP" TM Brand saran film. In the test, the same roll of "SARAN WRAP" was retracted by the laser beam along the crown and also at the indicated and explained offset positions, a+, b+, a— and b—, respectively as well as at (along the crown) a further scanning to exhibit the effect of "tail fluff" in the roll in a position designated as 46z. The graphical results are set forth in FIG. 6, which also shows the results of a control run in Curve C.

The results obtained are important insofar as they demonstrate that perfect alignment with the roll crown is not an absolute necessity in order to achieve and obtain reliable wrinkle data. Especially when higher scan speeds are brought into play, this is of crucial significance in that maintenance of perfect crown-impinging alignment becomes more difficult under such conditions. In other words, when high-speed scanning is utilized, some deviation from precise crown impingement by the laser beam may be tolerated without loss of effectiveness, accuracy or reliability in the quality control procedure of the present invention.

Another beneficial technique to utilize for betterment of constancy in reflected beam readings follows the illustration in FIG. 7 of the Drawing. Thus, use of many of the so-called "far field" photo-cell detectors having 3° head capabilities give, in actual practice, very different and difficult to reconcile results for two scans of the same rolls, for example, taken at displacements one from another as slight as only, say 0.020 inch (ca. 0.0508 centimeter). To overcome this with utilization of a nominal 1 inch (ca. 2.54 centimeters) diameter photo-resistive cell, it is quite beneficial to mask the cell (as is demonstrated in dimensionless fashion in FIG. 7) to better enable it to accurately pick up scattered light for about ½ inch (ca. 1.27 centimeter) on each side of the crown of the roll against which the cell is directed for reflected light to be gathered in its deflection from the roll. A useful slit size (unnumbered but shown in FIG. 7) for such a 1-inch cell is approximately ⅛th inch (ca. 0.3175 centimeter) in width extending across the full inch diameter of the cell face.

An exceptionally effective photo-detector unit to utilize is a so-called "solar cell" having a curved face surface in at least relative conformity to the curvature of the roll being tested. Such a unit is schematically portrayed in FIGS. 8 and 9 of the Drawing; and, with equivalent advantage, can also be masked (as illustrated in the angulated front elevation of the cell face shown in FIG. 9) to facilitate reflected beam collection and gathering from the roll under inspection. The response from a voltiac solar cell is quite analogous to that of the conventional photo-cells that are well adapted to utilization in the practice of the invention.

Assemblies in accordance with the present invention are adapted to inspect and operate at considerably high speeds. This is illustrated in the graphical representations of FIGS. 10 through 13, inclusive, of the Drawing demonstrating test results with rolls being tested with scan speed approaching 0.2 second/foot of roll length and using an RCA SQ 4403 photo-resistive cell for detection. In the several views of FIGS. 10-13, the various detected wrinkle, etc., points $W_1$, $W_2$, $W_3$ and $W_4$ are brought forth in the curves (each identified by reference numeral 60 on the chart paper replications designated 44). The tests portrayed also revealed that the photo-resistive cell has a much faster response than expected; this being in the neighborhood of ~2000 Hz rather than the sometimes indicated level of only 400–600 Hz. In any event, the operable maximum scan speeds usually far exceed (generally by a factor of about 2) commonly-utilized line speeds for wound plastic film supply roll production which typically are on the order of about 160 feet/minute of wound roll product output. Thus, there is no slow-down necessity in conventional manufacturing operations in order to apply and utilize the defect-inspecting and -detecting means of the present invention.

In this connection, by means of known implementation programming and handling techniques possible with adaptation of computerized and other electronic circuitry and associated mechanically responsive selection apparatus, it is possible with embodiments of the present invention to have the culling of imperfect and undesired roll product made completely automatic and without necessity for manual intervention or participation. Thus, on location of an objectionable defect in a given roll in the production line, a computer-actuated mechanical reject implementation can be actuated to remove an undesirable roll from the production line on receipt in the circuitry and mechanism of a detected-objectionable-defect signal via the laser beam reflection and gathering step followed, thereupon and thereafter, by apt intelligence signal handling and interpretation all by automatically responding and appropriately actuating means and devices.

The general procedures and principles of the present invention may be, if desired and with appropriate modification and change, extended and adapted to analogous inspection of unwound single- or multiply-layered supplies of flat sheet or film stock of plastic materials; this including such advantageous applications as on-line testings for defects in not only the individual involved layers but imperfections in layer-to-layer adhesion in multilayer structures and products not put out in supply roll from.

Many changes and modifications can readily be made in and adapted to embodiments and practices in accordance with the present invention without substantially departing from its apparent and intended spirit and scope, all in pursurance and accordance with same as it is set forth and delineated in the Claims hereto appended.

What is claimed is:

1. In cooperative combination assembly as a system for quality control test detection of wrinkle and other imperfections in a plastic film supply roll without physical contact or destruction thereof:
   (a) a multiple-layered, convolutely wound supply roll of a plastic film, the roll having a core upon which the plastic film is wound;
   (b) means for mounting said supply roll in longitudinally-extending disposition along its axial center line in the assembly;
   (c) means for generating a laser beam of electromagnetic radiation at a given wave length;
   (d) means for generating said laser beam into said supply roll along a path that is incident to and at a predetermined angle of orientation with respect to said supply roll so as to impinge at least substantially through and within a normal, upright plane that at least about intersects said center line of said supply roll; such that
      (i) any portion of said laser beam which passes through the multiple layers of said supply roll unobstructed by wrinkles or analogous structurally imperfect defects in or within the multiple film layers therein does so along a predictable and precisely deflected and reflected and unimpeded path; and
      (ii) any portion of said laser beam which impinges one of said wrinkles or the like defects is thereby scattered along predictable scattering paths including paths different than said unimpeded path;
   (e) means for picking up and indicating the unimpeded and impeded laser beam reflections whereby to detect and indicate through an intelligent reporting appliance any of said scattered electromagnetic radiations caused by said wrinkle and the like impediment(s); and
   (f) means for causing said laser beam to longitudinally sweep and scan the longitudinal length of said supply roll.

2. An assembly in accordance with that of claim 1, wherein said means (b) for mounting said supply roll (a) are fixed.

3. An assembly in accordance with that of claim 1, wherein said means (b) for mounting said supply roll (a) are movable and adapted to pass each mounted supply roll longitudinally along its axial center line thereupon and thereover.

4. An assembly in accordance with that of claim 1, wherein said laser beam generating means (c) is movable in a path parallel to the axial center line of said roll (a) so as to be adapted to longitudinally scan the roll along its upper peripheral surface in traverse at least approximately in the tangent line thereupon.

5. An assembly in accordance with that of claim 1, wherein said laser beam generating means (c) is fixed and said supply roll (a) is provided by said mounting means (b) therefor to be longitudinally movable under said beam so as to adapt said beam to longitudinally scan the roll along its upper peripheral surface while said roll is passing in traverse under said beam so that said beam sweeps the roll in at least approximately the tangent line upon the upper roll surface.

6. An assembly in accordance with that of claim 1, wherein said indicating element of means (e) is a recording means.

7. An assembly in accordance with that of claim 1, wherein said laser beam picking-up element of means (e) is a photo-resistive cell responsive to the electromagnetic radiations in a laser beam.

8. An assembly in accordance with that of claim 1, wherein said laser beam picking-up element of means (e) is a voltaic solar cell responsive to the electromagnetic radiations in a laser beam.

9. An assembly in accordance with any one of the assemblies of claims 1-8, inclusive, wherein same is installed in a production line set up for the manufacture of wound film supply roll (a) product.

10. An assembly in accordance with that of claim 9 and including, in addition thereto and further combination therewith means for automatically ejecting from the production line so as to reject therefrom any defective and quality control test-failing roll (a) upon signal indicated in and by said means (e) of objectionable wrinkle and the like flaw impediment(s) in any given imperfect roll.

11. In cooperative combination assembly as a system for quality control test detection of wrinkle and other imperfections in a plastic film supply roll without physical contact or destruction thereof:
   (a) a multiple-layered, convolutely wound supply roll of a plastic film;
   (b) means for mounting said supply roll in longitudinally-extending disposition along its axial center line in the assembly;
   (c) means for generating a laser beam of electromagnetic radiation at a given wave length;
   (d) means for generating said laser beam into said supply roll along a path that is incident to and at a predetermined angle of orientation with respect to said supply roll so as to impinge at least substantially through and within a normal, upright plane that at least about intersects said center line of said supply roll; such that
      (i) any portion of said laser beam which passes through the multiple layers of said supply roll unobstructed by wrinkles or analogous structurally imperfect defects in or within the multiple film layers therein does so along a predictable and precisely deflected and reflected and unimpeded path; and (ii) any portion of said laser beam which impinges one of said wrinkles or the like defects is thereby scattered along predictable scattering paths including paths different than said unimpeded path;

(e) means for picking up and indicating the unimpeded and impeded laser beam reflections whereby to detect and indicate through an intelligent reporting applicance any of said scattered electromagnetic radiations caused by said wrinkle and the like impediment(s) wherein said laser beam picking-up element of means (e) is a photo-resistive cell responsive to the electromagnetic radiations in a laser beam, the face of the cell being substantially masked across its central width so as to enable it to more selectively and accurately pick up and respond to the electromagnetic radiations from the reflected laser beam which it is gathering; and (f) means for causing said laser beam to longitudinally sweep and scan the longitudinal length of said supply roll.

12. In cooperative combination assembly as a system for quality control test detection of wrinkle and other imperfections in a plastic film supply roll without physical contact or destruction thereof:

(a) a multiple-layered, convolutely wound supply roll of a plastic film;

(b) means for mounting said supply roll in longitudinally-extending disposition along its axial center line in the assembly;

(c) means for generating a laser beam of electromagnetic radiation at a given wave length;

(d) means for generating said laser beam into said supply roll along a path that is incident to and at a predetermined angle of orientation with respect to said supply roll so as to impinge at least substantially through and within a normal, upright plane that at least about intersects said center line of said supply roll; such that (i) any portion of said laser beam which passes through the multiple layers of said supply roll unobstructed by wrinkles or analogous structurally imperfect defects in or within the multiple film layers therein does so along a predictable and precisely deflected and reflected and unimpeded path; and (ii) any portion of said laser beam which impinges one of said wrinkles or the like defects is thereby scattered along predictable scattering paths including paths different than said unimpeded path;

(e) means for picking up and indicating the unimpeded and impeded laser beam reflections whereby to detect and indicate through an intelligent reporting applicance any of said scattered electromagnetic radiations caused by said wrinkle and the like impediment(s) wherein said laser beam picking-up element of means (e) is a voltaic solar cell responsive to the electromagnetic radiations in a laser beam; the face of the involved cell is substantially masked across its central width so as to enable it to more selectively and accurately pick up and respond to the electromagnetic radiations from the reflected laser beam which it is gathering.

13. In cooperative combination assembly as a system for quality control test detection of wrinkle and other imperfections in a plastic film supply roll without physical contact or destruction thereof;

(a) a multiple-layered, convolutely wound supply roll of a plastic film;

(b) means for mounting said supply roll in longitudinally-extending disposition along its axial center line in the assembly;

(c) means for generating a laser beam of electromagnetic radiation at a given wave length;

(d) means for generating said laser beam into said supply roll along a path that is incident to and at a predetermined angle of orientation with respect to said supply roll so as to impinge at least substantially through and within a normal, upright plane that at least about intersects said center line of said supply roll; such that (i) any portion of said laser beam which passes through the multiple layers of said supply roll unobstructed by wrinkles or analogous structurally imperfect defects in or within the multiple film layers therein does so along a predictable and precisely deflected and reflected and unimpeded path; and (ii) any portion of said laser beam which impinges one of said wrinkles or the like defects is thereby scattered along predictable scattering paths including paths different than said unimpeded path;

(e) means for picking up and indicating the unimpeded and impeded laser beam reflections whereby to detect and indicate through an intelligent reporting applicance any of said scattered electromagnetic radiations caused by said wrinkle and the like impediment(s) wherein said laser beam picking-up element of means (e) is a photo-resistive cell responsive to the electromagnetic radiations in a laser beam; the face of the involved cell is curvilinear in contour so as to be in general correspondence to the involved curvature of the film supply roll (a) being tested; and (f) means for causing said laser beam to longitudinally sweep and scan the longitudinal length of said supply roll.

14. In cooperative combination assembly as a system for quality control test detection of wrinkle and other imperfections in a plastic film supply roll without physical contact or destruction thereof:

(a) a multiple-layered, convolutely wound supply roll of a plastic film;

(b) means for mounting said supply roll in longitudinally-extending disposition along its axial center line in the assembly;

(c) means for generating a laser beam of electromagnetic radiation at a given wave length;

(d) means for generating said laser beam into said supply roll along a path that is incident to and at a predetermined angle of orientation with respect to said supply roll so as to impinge at least substantially through and within a normal, upright plane that at least about intersects said center line of said supply roll; such that (i) any portion of said laser beam which passes through the multiple layers of said supply roll unobstructed by wrinkles or analogous structurally imperfect defects in or within the multiple film layers therein does so along a predictable and precisely deflected and reflected and unimpeded path; and (ii) any portion of said laser beam which impinges one of said wrinkles or the like defects is thereby scattered along predictable scattering paths including paths different than said unimpeded path;

(e) means for picking up and indicating the unimpeded and impeded laser beam reflections whereby to detect and indicate through an intelligent reporting appliance any of said scattered electromagnetic radiations caused by said wrinkle and the like impediment(s) wherein said laser beam picking-up element of means (e) is a voltaic solar cell responsive to the electromagnetic radiations in a laser beam, the face of the involved cell is curvilinear in contour so as to be in general correspondence to the involved curvature of the film supply roll (a) being tested;

(f) means for causing said laser beam to longitudinally sweep and scan the longitudinal length of said supply roll.

* * * * *